US011304683B2

(12) United States Patent
Mitra et al.

(10) Patent No.: US 11,304,683 B2
(45) Date of Patent: Apr. 19, 2022

(54) BIOPSY WORKFLOW USING MULTIMODAL IMAGING

(71) Applicant: General Electric Company, Schenectady, NY (US)

(72) Inventors: Jhimli Mitra, Nisayuna, NY (US); Thomas Kwok-Fah Foo, Clifton Park, NY (US); Desmond Teck Beng Yeo, Clifton Park, NY (US); David Martin Mills, Niskayuna, NY (US); Soumya Ghose, Niskayuna, NY (US); Michael John MacDonald, Albany, NY (US)

(73) Assignee: General Electric Company, Schenectady, NY (US)

( * ) Notice: Subject to any disclaimer, the term of this patent is extended or adjusted under 35 U.S.C. 154(b) by 290 days.

(21) Appl. No.: 16/570,859

(22) Filed: Sep. 13, 2019

(65) Prior Publication Data

US 2021/0077077 A1   Mar. 18, 2021

(51) Int. Cl.
*A61B 8/08* (2006.01)
*A61B 5/055* (2006.01)
(Continued)

(52) U.S. Cl.
CPC ............ *A61B 8/5261* (2013.01); *A61B 5/055* (2013.01); *A61B 5/7267* (2013.01);
(Continued)

(58) Field of Classification Search
CPC ..... A61B 8/5261; A61B 5/055; A61B 5/7267; A61B 10/0241; G06T 2207/20081;
(Continued)

(56) References Cited

U.S. PATENT DOCUMENTS 8,337,434 B2   12/2012   Vaezy et al.
10,188,361 B2   1/2019   Geiger et al.
(Continued)

OTHER PUBLICATIONS

Hegde et al., "Multiparametric MRI of Prostate Cancer: An Update on State-Of-The-Art Techniques and Their Performance in Detecting and Localizing Prostate Cancer", Journal of Magnetic Resonance Imaging, vol. 37, Issue: 5, pp. 1035-1054, May 2013, 33 pages.

(Continued)

*Primary Examiner* — Jason M Ip

(57) ABSTRACT

The subject matter discussed herein relates to multi-modal image alignment to facilitate biopsy procedures and post-biopsy procedures. In one such example, prostate structures (or other suitable anatomic features or structures) are automatically segmented in pre-biopsy MR and pre-biopsy ultrasound images. Thereafter, pre-biopsy MR and pre-biopsy ultrasound contours are aligned. To account for non-linear deformation of the imaged anatomic structure, a patient-specific transformation model is trained via deep learning based at least in part on the pre-biopsy ultrasound images. The pre-biopsy ultrasound images that are overlaid with the pre-biopsy MR contours and based off the deformable transformation model are then aligned with the biopsy ultrasound images. Such real-time alignment using multi-modality imaging techniques provides guidance during the biopsy and post-biopsy system.

14 Claims, 4 Drawing Sheets

(51) Int. Cl.
- *A61B 5/00* (2006.01)
- *A61B 10/02* (2006.01)
- *G06T 7/33* (2017.01)
- *G16H 50/20* (2018.01)
- *G16H 30/40* (2018.01)

(52) U.S. Cl.
CPC .......... *A61B 10/0241* (2013.01); *G06T 7/344* (2017.01); *G16H 30/40* (2018.01); *G16H 50/20* (2018.01); *G06T 2207/10088* (2013.01); *G06T 2207/10136* (2013.01); *G06T 2207/20081* (2013.01); *G06T 2207/30081* (2013.01); *G06T 2207/30096* (2013.01)

(58) Field of Classification Search
CPC . G06T 2207/30081; G06T 2207/10088; G06T 2207/10136; G06T 7/344; G16H 50/20; G16H 30/40
See application file for complete search history.

(56) References Cited

U.S. PATENT DOCUMENTS

| | | | |
|---|---|---|---|
| 2007/0167705 | A1 | 7/2007 | Chiang et al. |
| 2011/0160566 | A1 | 6/2011 | Petropoulos et al. |
| 2012/0071749 | A1* | 3/2012 | Xu ........................ A61B 8/0833 600/411 |
| 2014/0073907 | A1 | 3/2014 | Kumar et al. |
| 2014/0275962 | A1* | 9/2014 | Foo ........................ A61N 5/1049 600/411 |
| 2017/0337682 | A1* | 11/2017 | Liao .......................... G06T 7/30 |

OTHER PUBLICATIONS

Taylor et al., "Comparison of Prostate Volume Measurements between Different Techniques and Modalities", The Royal Australian and New Zealand College of Radiologist, pp. 01-16, Oct. 25-28, 2014, 16 pages.

Camps et al., "The Use of Ultrasound Imaging in the External Beam Radiotherapy Workflow of Prostate Cancer Patients", Biomedical Research International, pp. 01-16, Jan. 24, 2018, 18 pages.

Balakrishnan et al., "VoxelMorph: A Learning Framework for Deformable Medical Image Registration", Cornell University, pp. 01-16, Jan. 17, 2019, 16 pages.

Sloun et al., "Deep Learning for Real-time, Automatic, and Scanner-adapted Prostate (Zone) Segmentation of Transrectal Ultrasound, for Example, Magnetic Resonance Imaging-transrectal Ultrasound Fusion Prostate Biopsy", European Urology Focus, pp. 01-08, Apr. 23, 2019, 8 pages.

* cited by examiner

BIOPSY WORKFLOW USING MULTIMODAL IMAGING

BACKGROUND

The subject matter disclosed herein relates to image alignment, and more particularly to systems and methods that utilize deformable transformation for image alignment.

Magnetic resonance imaging (MRI) is becoming more important for guided intervention and therapy since it provides soft tissue contrast that enables mapping of the location and boundary of pathological tissue (e.g., tumors) in the planning/diagnosis phases. However, due to the limited patient space in the magnet bore and low imaging frame rate, it is difficult to integrate real-time MRI into interventional and therapy workflows. Thus, real-time MR images are typically not available in the interventional/treatment phase, which increases the risks of invasive access or treatment of healthy tissue regions that were not targeted in the planning phase. In addition, clinicians may fail to completely access or treat the pathological tissue due to the lack of real-time tracing of pathological tissue boundaries. While segmentation or manual tracing of a lesion/tumor from MR images in the planning phase may provide an initial location of the fiducial, due to physiological motion, this initial location may not be the true position of the target lesion/tumor.

Ultrasound imaging may provide real-time imaging. However, ultrasound imaging provides poorer soft tissue contrast, which limits the ability to locate or delineate pathology or target lesions. Linking real-time ultrasound imaging with pre-acquired MR images (acquired at a different time) is time-consuming, computationally intensive, and may have inaccuracies that adversely affects the precision and outcome of the intervention procedure. In addition, image contrast and spatial resolution in MRI and ultrasound imaging are different and that exacerbates the difficulty in aligning or registering MRI and ultrasound images. Thus, there is a need for an imaging approach that provides sufficient soft tissue contrast during the intervention/treatment phase while also providing real-time positional information of the target lesion.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a multi-modal imaging method for generating a patient-specific transformation model is provided. In accordance with this method, pre-biopsy magnetic resonance (MR) image data and pre-biopsy ultrasound image data of a patient are acquired simultaneously or one after the other. An anatomic region of interest and one or more lesions in an MR volume generated from the MR image data are segmented. The anatomic region of interest in an ultrasound volume generated from the ultrasound image data is also segmented. Contours of the segmented anatomic region of interest in the MR volume are aligned with corresponding contours of the anatomic region of interest in the ultrasound volume to generate a pre-biopsy volume in which the MR volume and the ultrasound volume are aligned and on which contours of the one or more lesions from the MR volume are aligned. A deep learning transformation model is trained based at least in part on the pre-biopsy ultrasound image data to create a deformable transformation model specific to the patient.

In a further embodiment, a multi-modal imaging system is provided. In accordance with this embodiment, the image system comprises memory encoding processor-executable routines and a processing component configured to access the memory and execute the processor-executable routines. The routines, when executed by the processing component, cause the processing component to perform actions that include at least: acquiring pre-biopsy magnetic resonance (MR) image data and pre-biopsy ultrasound image data of a patient; segmenting an anatomic region of interest and one or more lesions in an MR volume generated from the MR image data; segmenting the anatomic region of interest in an ultrasound volume generated from the ultrasound image data; aligning contours of the segmented anatomic region of interest in the MR volume with corresponding contours of the anatomic region of interest in the ultrasound volume to generate a pre-biopsy volume in which the MR volume and the ultrasound volume are aligned and on which contours of the one or more lesions from the MR volume are aligned; training a deep learning transformation model based at least in part on the pre-biopsy ultrasound image data to create a deformable transformation model specific to the patient; acquiring one or more biopsy ultrasound images of the patient during a biopsy procedure; performing a deformable alignment using the deformable transformation model to align each biopsy ultrasound image with the pre-biopsy volume, wherein the contours of the one or more lesions associated with the pre-biopsy volume are aligned with each biopsy ultrasound image; and providing a real-time visualization of the contours of the one or more lesions on at least one of the biopsy ultrasound images.

In an additional embodiment, a method to register a real-time image for a biopsy system is provided. In accordance with this method, one or more biopsy ultrasound images of a patient are acquired during a biopsy procedure. A deformable alignment is performed using a deformable transformation model to align each biopsy ultrasound image with a pre-biopsy volume. The deformable transformation is specific to the patient and the contours of one or more lesions are associated with each biopsy ultrasound image. A real-time visualization is provided of the contours of the one or more lesions on some or all of the biopsy ultrasound images.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
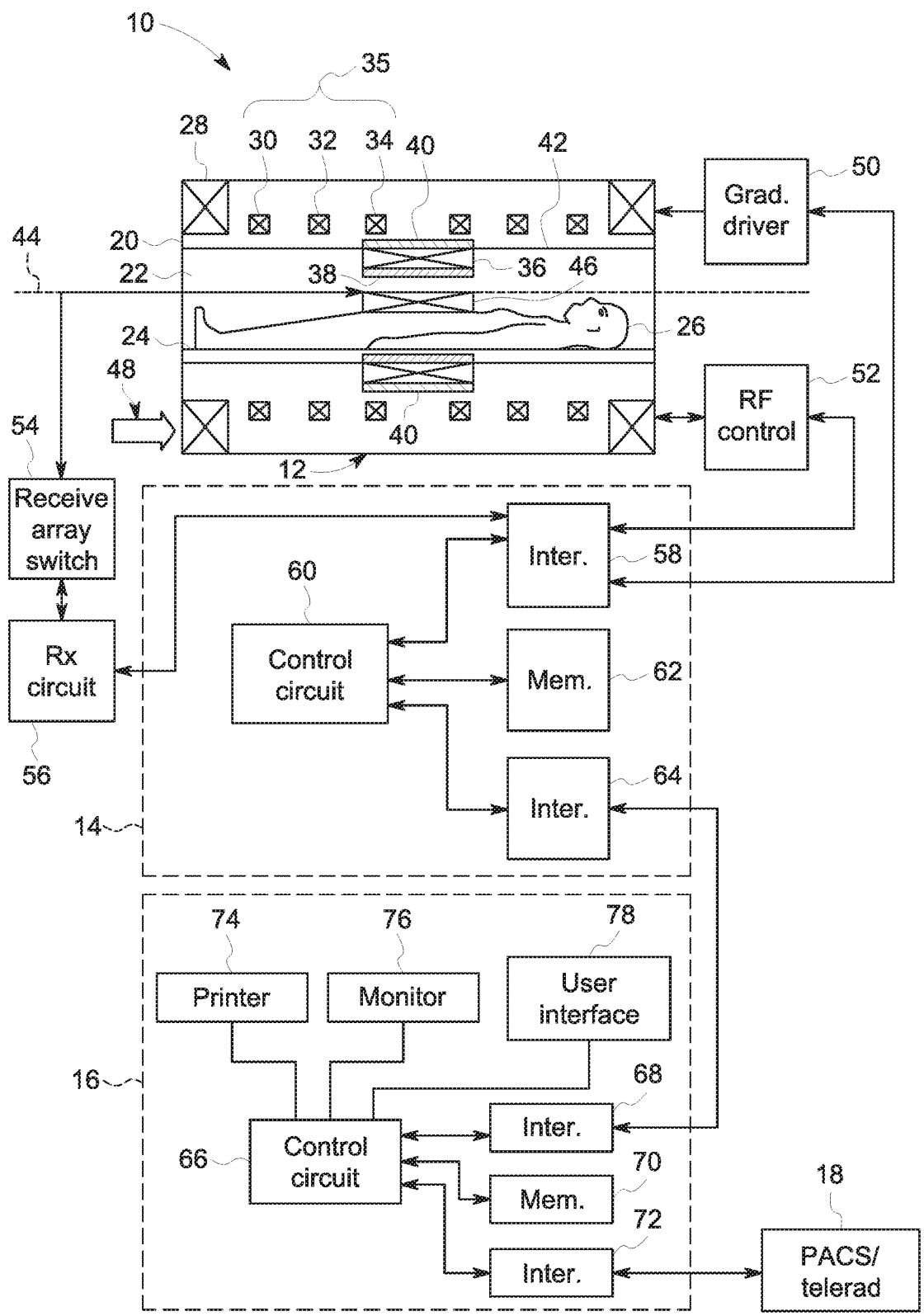
FIG. 1 illustrates a magnetic resonance imaging (MRI) system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided for both general context for aspects of the present disclosure and to facilitate understanding and explanation of certain of the technical concepts described herein.

As discussed herein, a process is disclosed that includes the simultaneous or near-simultaneous (e.g., temporally consecutive) acquisition of MR and transabdominal ultrasound (TAUS) prostate images in a pre-biopsy phase. Use of transabdominal prostate imaging offers certain benefits relative to transrectal ultrasound (TRUS) imaging, such as improved patient comfort and absence of deformation of the prostate due to TRUS probe insertion. Hence, between the diagnostic or pre-biopsy MRI and the ultrasound-guided biopsy procedure, deformation of the prostate is avoided, which simplifies the multimodal deformable alignment of the prostate. The pre-biopsy TAUS image data is integrated with information derived from the pre-biopsy MR imaging, which provides useful prostate tissue contrast and is also a useful diagnostic tool for assessing prostate disease. Thus, unlike prior approaches, the present disclosure includes simultaneous or near-simultaneous pre-biopsy MR and TAUS imaging, which is then leveraged for guidance in a prostate biopsy context.

With the preceding in mind, material related to imaging techniques and terms is provided below so as to impart some familiarity with such imaging systems and to provide useful real-world context for other aspects of the disclosure. With respect to magnetic resonance imaging (MRI) systems, and turning to FIG. 1 where one such system is schematically illustrated for reference, interactions between a primary magnetic field, time varying magnetic gradient fields, and a radiofrequency (RF) field with gyromagnetic material(s) within a subject of interest (e.g., a patient) are used to generate images or volumetric representations of structural and/or functional relationships within the patient. Gyromagnetic materials, such as hydrogen nuclei in water molecules, have characteristic behaviors in response to externally applied electromagnetic fields (e.g., constant or time varying electric fields, magnetic fields, or a combination thereof) that may be leveraged in this manner. For example, the precession of spins of these nuclei can be influenced by manipulation of the fields to produce RF signals that can be detected, processed, and used to reconstruct a useful image.

With this in mind, and referring to FIG. 1, a magnetic resonance imaging system 10 is illustrated schematically as including a scanner 12, scanner control circuitry 14, and system control circuitry 16. The imaging system 10 additionally includes remote access and storage systems 18 and/or devices such as picture archiving and communication systems (PACS), or other devices such as teleradiology equipment so that data acquired by the imaging system 10 may be accessed on- or off-site. While the imaging system 10 may include any suitable scanner or detector, in the illustrated embodiment, the imaging system 10 includes a full body scanner 12 having a housing 20 through which an opening (e.g., an annular opening) is formed to accommodate a patient bore 22. The patient bore 22 may be made of any suitable material such as a non-metallic and/or non-magnetic material and generally includes components of the scanner 12 proximate to a subject. A table 24 is movable into the patient bore 22 to permit a patient 26 to be positioned therein for imaging selected anatomy within the patient 26. As described herein, the patient bore 22 may include one or more bore tubes to support various components of the scanner 12 and/or the patient 26. In some embodiments, the patient bore 22 may support the table 24 and/or articulation components (e.g., a motor, pulley, and/or slides).

The scanner 12 may include a series of associated superconducting magnetic coils for producing controlled electromagnetic fields for exciting the gyromagnetic material within the anatomy of the subject being imaged. Specifically, a primary magnet coil 28 is provided for generating a primary magnetic field, which is generally aligned with an axis 44 of the patient bore 22. A series of gradient coils 30, 32, and 34 (collectively 35) permit controlled magnetic gradient fields to be generated for positional encoding of certain of the gyromagnetic nuclei within the patient 26 during examination sequences. An RF coil 36 is configured to generate radio frequency pulses for exciting the certain gyromagnetic nuclei within the patient 26. In accordance with an aspect of the present disclosure, the RF coil 36 may be implemented on a coil support tube 38 defining at least a portion of the patient bore 22. Further, an RF shield 40 may be implemented on a shield support tube 42 also defining at least a portion of the patient bore 22 to reduce electromagnetic interference within the imaging system 10, as well as devices separate from the imaging system 10. In addition to the coils that may be local to the scanner 12, the imaging system 10 may also include a set of receiving coils 46 (e.g., an array of coils) configured for placement proximal (e.g., against) to the patient 26. As an example, the receiving coils 46 can include cervical/thoracic/lumbar (CTL) coils, head coils, single-sided spine coils, and so forth. Generally, the receiving coils 46 are placed close to or on top of the patient 26 so as to receive the weak RF signals (e.g., weak relative to the transmitted pulses generated by the scanner coils) that are generated by certain of the gyromagnetic nuclei within the patient 26 as they return to their relaxed state. In some embodiments, the RF coils 36 may both transmit and receive RF signals accomplishing the role of the receiving coils 46.

The various coils of the imaging system 10 are controlled by external circuitry to generate the desired field and pulses, and to read emissions from the gyromagnetic material in a controlled manner. In the illustrated embodiment, a main power supply 48 provides power to the primary magnetic coil 28 to generate the primary magnetic field. A driver circuit 50 may include amplification and control circuitry for supplying current to the coils as defined by digitized pulse sequences output by the scanner control circuitry 14.

An RF control circuit 52 is provided for regulating operation of the RF coil 36. The RF control circuit 52 includes a switching device for alternating between the active and inactive modes of operation, wherein the RF coil 36 transmits and does not transmit signals, respectively. The RF control circuit 52 may also include amplification circuitry to generate the RF pulses. Similarly, the receiving coils 46, or RF coils 36 if no separate receiving coils 46 are implemented, are connected to a switch 54, which is capable of switching the receiving coils 46 between receiving and non-receiving modes. Thus, the receiving coils 46 may resonate with the RF signals produced by relaxing gyromagnetic nuclei from within the patient 26 while in the receiving mode, and avoid resonating with RF signals while in the non-receiving mode. Additionally, a receiving circuit 56 may receive the data detected by the receiving coils 46 and may include one or more multiplexing and/or amplification circuits.

It should be noted that while the scanner 12 and the control/amplification circuitry described above are illustrated as being connected by single lines, one or more cables or connectors may be used depending on implementation. For example, separate lines may be used for control, data communication, power transmission, and so on. Further, suitable hardware may be disposed along each type of line for the proper handling of the data and current/voltage. Indeed, various filters, digitizers, and processors may be disposed between the scanner 12 and the scanner control circuitry 14 and/or system control circuitry 16.

As illustrated, the scanner control circuitry 14 includes an interface circuit 58, which outputs signals for driving the gradient coils 35 and the RF coil 36 and for receiving the data representative of the magnetic resonance signals produced in examination sequences. The interface circuit 58 may be connected to a control and analysis circuit 60. The control and analysis circuit 60 executes the commands to the driver circuit 50 and RF control circuit 52 based on defined protocols selected via system control circuitry 16.

The control and analysis circuit 60 may also serve to receive the magnetic resonance signals and perform subsequent processing before transmitting the data to system control circuitry 16. Scanner control circuitry 14 may also include one or more memory circuits 62, which store configuration parameters, pulse sequence descriptions, examination results, and so forth, during operation.

A second interface circuit 64 may connect the control and analysis circuit 60 to a system control circuit 66 for exchanging data between scanner control circuitry 14 and system control circuitry 16. The system control circuitry 16 may include a third interface circuit 68, which receives data from the scanner control circuitry 14 and transmits data and commands back to the scanner control circuitry 14. As with the control and analysis circuit 60, the system control circuit 66 may include a computer processing unit (CPU) in a multi-purpose or application specific computer or workstation. System control circuit 66 may include or be connected to a second memory circuit 70 to store programming code for operation of the imaging system 10 and to store the processed image data for later reconstruction, display and transmission. The programming code may execute one or more algorithms that, when executed by a processor, are configured to perform reconstruction of acquired data or other operations involving the acquired data.

An additional input output (I/O) interface 72 may be provided for exchanging image data, configuration parameters, and so forth with external system components such as remote access and storage systems 18. Finally, the system control circuit 66 may be communicatively coupled to various peripheral devices for facilitating an operator interface and for producing hard copies of the reconstructed images. In the illustrated embodiment, these peripherals include a printer 74, a monitor 76, and a user interface 78 including, for example, devices such as a keyboard, a mouse, a touchscreen (e.g., integrated with the monitor 76), and so forth.

In operation, a user (e.g., a radiologist) may configure and/or oversee control of the imaging system 10. Additionally, the user may assist in positioning the subject (e.g., a patient 26) within the patient bore 22. In some embodiments, the patient bore 22 may surround an entire subject or just a portion thereof (e.g., a patient's head, thorax, and/or extremity) while an imaging session is performed.

Figure 2:
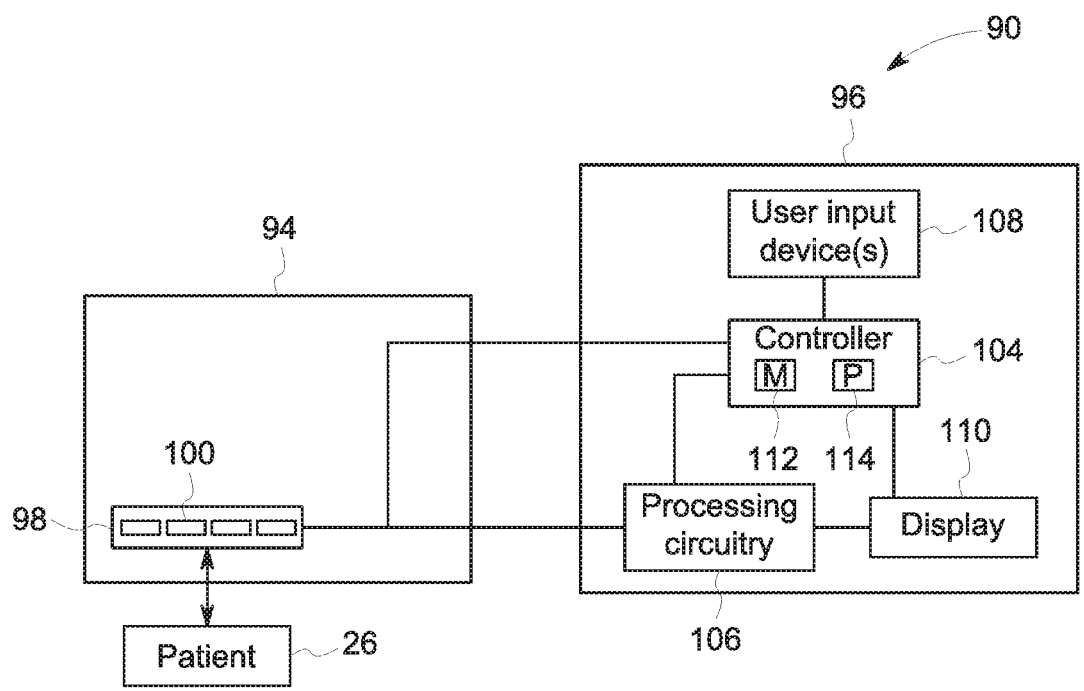
FIG. 2 is an embodiment of a block diagram of an ultrasound system, in accordance with aspects of the present disclosure.

In addition to a MRI imaging system, certain examples discussed herein also utilize ultrasound data acquisition, such as to generate ultrasound images of the same anatomy of interest scanned using an MRI system 10. With this in mind, and to provide familiarity with aspects of such an ultrasound imaging system, FIG. 2 illustrates a block diagram of an embodiment of an ultrasound imaging system 90 capable of acquiring ultrasound data of a patient undergoing imaging, including during an interventional procedure, such as a biopsy. In the illustrated embodiment, the ultrasound system 90 is a digital acquisition and beam former system, but in other embodiments, the ultrasound system 90 may be any suitable type of ultrasound system, not limited to the illustrated type. The ultrasound system 90 may include the ultrasound probe 94 and a workstation 96 (e.g., monitor, console, user interface) which may control operation of the ultrasound probe 94 and may process image data acquired by the ultrasound probe 94. The ultrasound probe 94 may be coupled to the workstation 96 by any suitable technique for communicating image data and control signals between the ultrasound probe 94 and the workstation 96 such as a wireless, optical, coaxial, or other suitable connection.

The ultrasound probe 94 contacts the patient 26 during an ultrasound examination. The ultrasound probe 94 may include a patient facing or contacting surface that includes a transducer array 98 having a plurality of transducer elements 100 capable of operating in a switched manner between transmit and receive modes. Each individual transducer element 100 may be capable of converting electrical energy into mechanical energy for transmission and mechanical energy into electrical energy for receiving. It should be noted that the transducer array 98 may be configured as a two-way transducer capable of transmitting ultrasound waves into and receiving such energy from a subject or patient 26 during operation when the ultrasound probe 94 is placed in contact with the patient 26. More specifically, the transducer elements 100 may convert electrical energy from the ultrasound probe 94 into ultrasound waves (e.g., ultrasound energy, acoustic waves) and transmit the ultrasound waves into the patient 26. The ultrasound waves may be reflected back toward the transducer array 98, such as from tissue of the patient 26, and the transducer elements 100 may convert the ultrasound energy received from the patient 26 (reflected signals or echoes) into electrical signals for processing by the ultrasound probe 94 and the workstation 96 to provide data that may be analyzed. The number of transducer elements 100 in the transducer array 98 and the frequencies at which the transducer elements 100 operate may vary depending on the application. In certain embodiments, the probe 94 may include additional elements not shown in FIG. 2, such as additional electronics, data acquisition, processing controls, and so forth.

As previously discussed, the ultrasound probe 94 is communicatively coupled to the workstation 96 of the ultrasound imaging system 90 to facilitate image collection and processing. As will be appreciated, the workstation 96 may include a number of components or features to control operation of the ultrasound probe 94, facilitate placement and/or guidance of the ultrasound probe 94, and facilitate production and/or interpretation of ultrasound data (including reconstructed ultrasound images). For instance, as illustrated, the workstation 96 may include a controller 104, processing circuitry 106, one or more user input devices 108, and a display 110. In certain embodiments, the workstation 96 may include additional elements not shown in FIG. 2, such as additional data acquisition and processing controls, additional image display panels, multiple user interfaces, and so forth.

The controller 104 may include a memory 112 and a processor 114. In some embodiments, the memory 112 may include one or more tangible, non-transitory, computer-readable media that store instructions executable by the processor 114 and/or data to be processed by the processor 114. For example, the memory 112 may include random access memory (RAM), read only memory (ROM), rewritable non-volatile memory such as flash memory, hard drives, optical discs, and/or the like. Additionally, the processor 114 may include one or more general purpose microprocessors, one or more application specific processors (ASICs), one or more field programmable logic arrays (FPGAs), or any combination thereof. The controller 104 may control transmission of the ultrasound waves into the patient 26 via the transducer array 98.

The processing circuitry 106 may include receiving and conversion circuitry. The processing circuitry 106 may receive the electrical signal data from the transducer array 98 of the ultrasound probe 94 representing reflected ultrasound energy returned from tissue interfaces within the patient 26. The processing circuitry 106 may process the data from the transducer array 98, such as correcting for noise artifacts, or the like. The processing circuitry 106 may then convert the signal data into an ultrasound image for presentation via the display 110. The controller 104 may cause display of the ultrasound image or images (or a construct or model generated based on such images or raw image data) produced by the processing circuitry 106 from the signal data received from the transducer array 98 of the ultrasound probe 94.

In operation, the controller 104 may receive a signal indicative of a target anatomy of the patient 26 and/or a target scan plane of the target anatomy via the one or more user input devices 108 of the workstation 96. The one or more user input devices 108 may include a keyboard, a touchscreen, a mouse, buttons, switches, or other devices suitable to allow the operator to input the target anatomy and/or the desired scan plane of the target anatomy. Based on the target anatomy and/or the target scan plane of the target anatomy, the controller 104 may output a signal to the transducer array 98 of the ultrasound probe 94 indicative of an instruction to convert the electrical energy from the ultrasound probe 94 into ultrasound waves and transmit the ultrasound waves into the patient 26 and to detect the ultrasound energy that is reflected back from the tissue interfaces within the patient 26.

Figure 3:
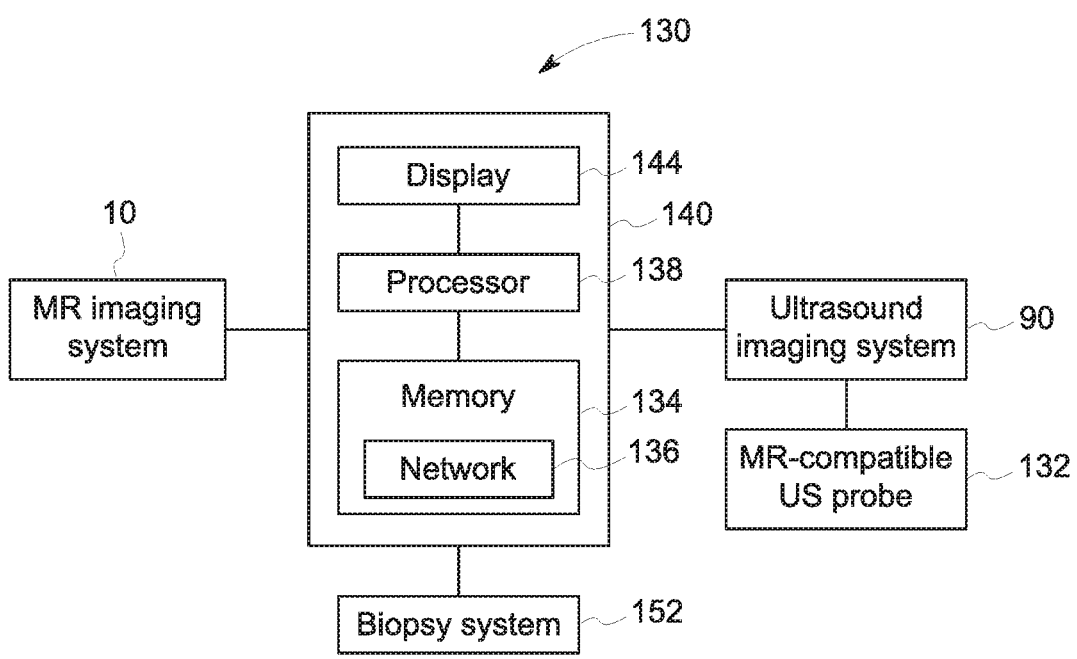
FIG. 3 depicts a schematic diagram of an embodiment of a combined magnetic resonance and ultrasound imaging system, in accordance with aspects of the present disclosure.

With the preceding comments in mind, FIG. 3 illustrates schematic diagram of an embodiment of a combined MR and ultrasound imaging system 130 that may be used for non-invasive motion management of radiation therapy, or other therapy or surgical or interventional procedures, as described herein. The combined MR and ultrasound imaging system 130 may be similar to the system described in U.S. patent application Ser. No. 15/870,519, entitled "Image-guided Biopsy Techniques", filed Jan. 12, 2018, which may be incorporated by reference in its entirety. The combined MR and ultrasound imaging system 130 includes a magnetic resonance (MR) imaging system 10 and an ultrasound imaging system 90. The ultrasound imaging system 90 may be communicatively coupled to a MR-compatible ultrasound probe 132. The MR-compatible ultrasound probe 132 may be an ultrasound probe configured for use in combination with the MR imaging system 10. As such, the MR-compatible ultrasound probe (as described in U.S. patent application Ser. No. 15/897,964, entitled "Magnetic Resonance Compatible Ultrasound Probe", filed Feb. 15, 2018, which may be incorporated by reference in its entirety) may contain low or no ferromagnetic material (e.g., iron, nickel, cobalt) content, as discussed in greater detail with reference to FIG. 1.

In order to facilitate a more simple workflow, the ultrasound probe 132 may be capable of three-dimensional (3D) volume acquisition with high temporal resolution, allowing an ultrasound image volume to be acquired at each time point. Moreover, besides being MR-compatible, the 3D ultrasound probe 132 may be electronically steerable and hands-free. This allows the ultrasound image field-of-view to be electronically manipulated, obviating the need for robotic or mechanical ultrasound probe holders to change the imaging field-of-view. In this manner, simultaneous MR and ultrasound images can be easily acquired. Moreover, during the interventional procedure (e.g., biopsy), the same ultrasound probe can be used and positioned in approximately the same manner as during the pre-interventional MR+ultrasound procedure without difficulty. This provides a further simplification of the workflow as approximately the same imaging set up is used between the pre-interventional and interventional procedure as the same ultrasound probe is utilized, and in the same manner. The data from the MR and ultrasound systems may be streamed to and stored in a memory system 134 which contains a trained network model 136, as discussed in greater detail herein, and which may be connected to other data storage or processing systems.

While the preceding describes relevant or utilized aspects of a combined imaging system as may be used prior to a procedure (e.g., pre-biopsy or other interventional procedure), other aspects of the system may be relevant or used during the procedure (e.g., biopsy). By way of example, during the procedure a biopsy system 152 may be present and may leverage information gathered using the combined imaging system 130. The biopsy system 152 in this example represents an interventional component that can, in other contexts, be a radiation therapy system, a surgical interventional system, or another medical interventional component. In some embodiments, the biopsy system 152 may be a trans-perineal biopsy system. The biopsy system 152, as discussed in greater detail below, may be guided by images obtained via the MR imaging system 10 in combination with images obtained via the ultrasound imaging system 90.

It should be noted that the system and process described herein entails two stages in the biopsy procedure or interventional procedure, a pre-biopsy stage (e.g., patient-specific planning stage) where simultaneous MR and ultrasound imaging occurs, and a biopsy stage or procedure (e.g., interventional/therapy phase) where ultrasound imaging occurs. With this in mind, the combined MR and ultrasound imaging system 130 may further include a system controller block 140 communicatively coupled to the other elements of the combined MR and ultrasound imaging system 130, including the MR imaging system 10, the ultrasound imaging system 90, and the therapy (e.g., biopsy) system 152. The controller 140 may include a memory 134 and a processor 138. In some embodiments, the memory 134 may include one or more tangible, non-transitory, computer-readable media that store instructions executable by the processor 138 and/or data to be processed by the processor 138. For example, the memory 134 may include random access memory (RAM), read only memory (ROM), rewritable non-volatile memory such as flash memory, hard drives, optical discs, and/or the like. Additionally, the processor 138 may include one or more general purpose microprocessors, one or more graphic processing units (GPUs), one or more application specific processors (ASICs), one or more field programmable logic arrays (FPGAs), or any combination thereof. Further, the memory 134 may store instructions executable by the processor 138 to perform the methods described herein. Additionally, the memory 134 may store images obtained via the MR imaging system 10 and the ultrasound imaging system 90 and/or algorithms utilized by the processor 138 to help guide the biopsy system 152 based on image inputs from the MR imaging system 10 and the ultrasound imaging system 14, as discussed in greater detail below. The memory 134 may also store a neural network 136 that when trained functions as an unsupervised deep learning-based deformable registration network as described in greater detail below. In certain embodiments, the system may be coupled to a remote database that includes the neural network 136 as opposed to directly incorporating the neural network 136. Further, the controller 140 may include a display 144 that may be used to display the images obtained by the MR imaging system 10 and the ultrasound imaging system 90.

It should be noted that the types of MR and ultrasound images acquired may vary. For efficiency and also to match acquisition frame rates, one embodiment has two-dimensional (2D) MR images acquired simultaneously with three-dimensional (3D) ultrasound images over time, i.e., matching time-series 2D MR images to time-series 3D ultrasound images at each time point. In this case, there is the possibility that endogenous fiducial structures/markers in the time-series 3D ultrasound images may not be common to the time-series 2D MR images. In certain embodiments, the MR images and/or ultrasound images may be stacked 2D images acquired over time.

Alternatively, sorting the time-series 2D MR images into corresponding collections, with each collection representing the same respiratory state, reformatted time-series 3D (4D) MR images that are temporally matched with the time-series 3D (4D) ultrasound images may be generated. This increases the probability that endogenous fiducial structures/markers in the ultrasound images are common in the MR images. However, even if this is not the case, the techniques disclosed below provide adequate matching or registration between MR and ultrasound images. In another embodiment, with sufficiently fast acquisition speeds, time-series 3D (4D) MR images are acquired simultaneously with time-series 3D (4D) ultrasound images to yield corresponding time-series 3D volume images that are temporally matched. As an MR image set at a reference time point and the corresponding ultrasound image volume are acquired at the same time point, the organ-of-interest visualized in MR and ultrasound have the same shape, orientation, and feature outlines, making the MR-to-ultrasound transformation an easier undertaking.

With the preceding in mind, and using a prostate biopsy example to provide a real-word context and to facilitate explanation, in conventional clinical practice only a pre-biopsy MR volume (with phased-array surface coils) is typically acquired. A pre-biopsy assessment of the prostate using a trans-rectal ultrasound (TRUS) probe is not typically performed. Instead, on the day of the biopsy procedure, the patient is subjected to two TRUS probe insertions. In the first TRUS procedure, a 2D sweep of the prostate is performed to reconstruct a 3D ultrasound volume of the prostate. The ultrasound volumes are subsequently aligned with the pre-biopsy MR volumes in a time-consuming process involving manual contouring of the prostate contours in both modalities. The second TRUS procedure is performed during the biopsy procedure and is used for image guidance. As may be appreciated, deformation due to patient positioning differences, physiological conditions like bowel filling or gas in rectum, and bladder filling between the pre-biopsy and biopsy imaging sessions may lead to difficulty in accurate integration of MR information and poor lesion localization for biopsy guidance.

As discussed in the present disclosure, a process is described that includes the simultaneous or near-simultaneous (e.g., temporally consecutive) acquisition of MR and trans-abdominal ultrasound (TAUS) prostate images in the pre-biopsy phase, such as may be acquired with a MR-compatible 3D ultrasound probe. Use of trans-abdominal prostate imaging, while not sufficient itself to diagnose malignancy, may still be sufficient to assess the prostate volume. Further, TAUS imaging may address certain issues related to TRUS imaging, such as patient discomfort and deformation of the prostate due to TRUS probe insertion. In accordance with the present disclosure, the pre-biopsy TAUS image data is integrated with information derived from the pre-biopsy MRI, which provides useful prostate tissue contrast and is also a useful diagnostic tool for assessing prostate disease. Thus, unlike prior approaches, the present disclosure includes simultaneous or near-simultaneous pre-biopsy MR and TAUS imaging, which is then leveraged for guidance in a prostate biopsy context. The TAUS probe provides patient comfort compared to TRUS, and does not deform the prostate due to probe insertion. In addition, in certain contexts trans-perineal biopsy may be employed instead of trans-rectal biopsy in order to reduce infection risk associated with increased bacteria in the rectum.

Figure 4:
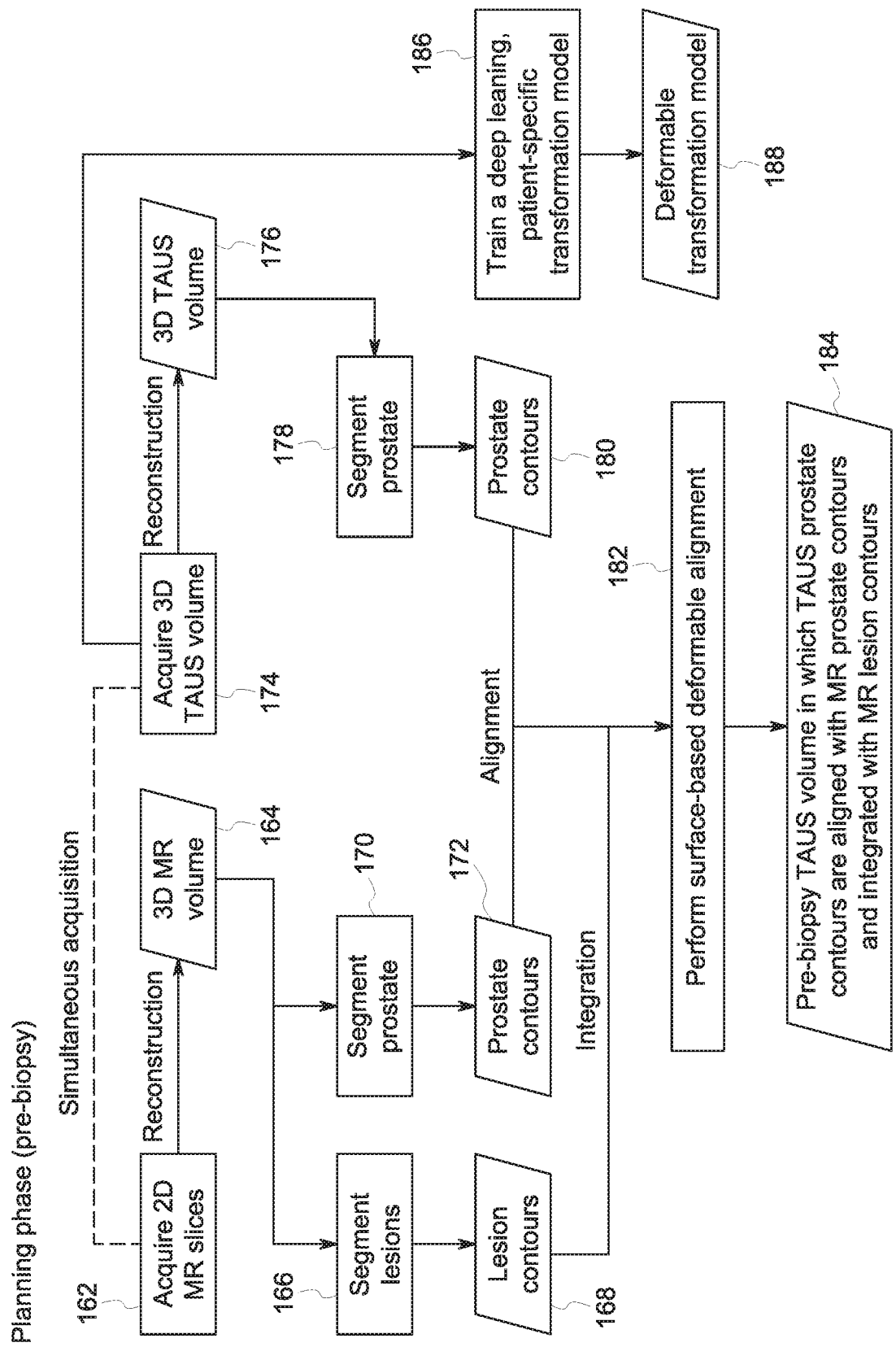
FIG. 4 illustrates an ultrasound-MRI fusion flowchart, in accordance with aspects of the planning phase of the present disclosure.
Figure 5:
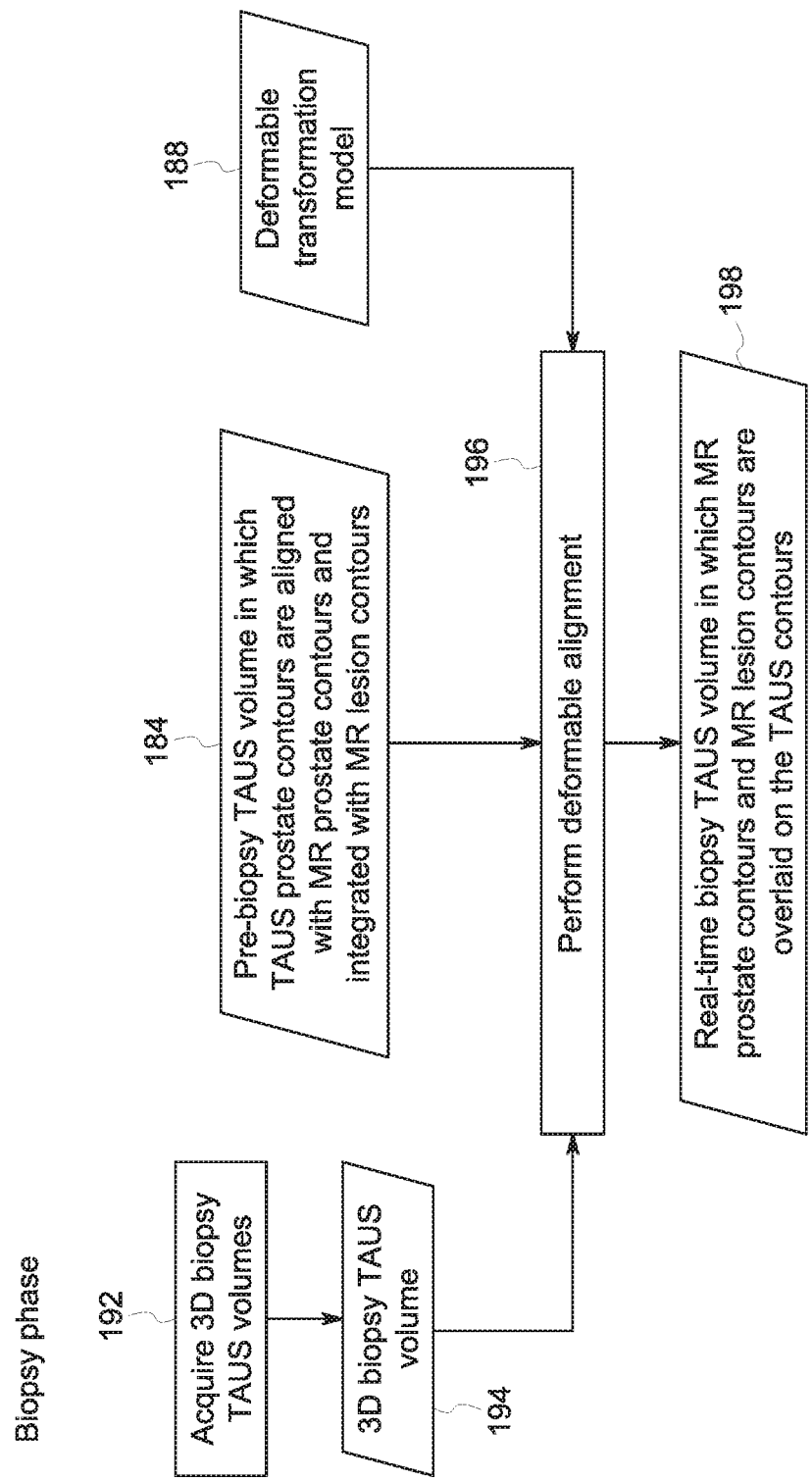
FIG. 5 illustrates an ultrasound-MRI fusion flowchart, in accordance with aspects of the biopsy phase of the present disclosure.

With the preceding in mind, and turning to FIGS. 4 and 5, a pair of workflows are depicted. During the planning phase (shown in FIG. 4), pre-biopsy 2D MR slices are acquired (step 162). These 2D MR slices are reconstructed into one or more 3D MR volumes 164. The anatomy of interest, such as the prostate, on the reconstructed 3D MR volume 164 is then segmented (step 170) by an automated segmentation method or manually by a radiologist. This segmentation step 170 results, in this example, in the prostate contours 172 being identified and/or labeled on the pre-biopsy reconstructed MR volume 164. Along with the prostate being segmented, lesions present in the reconstructed 3D MR volume 164 are also segmented (step 166) by an automated segmentation method or manually by a radiologist. Though shown as a separate segmentation step for simplicity and to facilitate explanation, it should be appreciated that the segmentation steps 166 and 170 may be the same segmentation operation (i.e., performed by the same automated routine or process or in the same manual evaluation step). Segmentation of lesions at step 166 results in the delineation of lesion contours 168 on the pre-biopsy reconstructed MR volume 164.

In parallel with or subsequent to (e.g., in temporally consecutive scans) the MR imaging, pre-biopsy 3D transabdominal ultrasound (TAUS) volumes are acquired (step 174) (such as using an MR compatible ultrasound probe). The 3D TAUS volumes may entail longitudinal volume frames and be a part of a pre-biopsy ultrasound image dataset. In the present example, these 3D TAUS volumes are reconstructed into one or more representative 3D TAUS volumes 176. The anatomy of interest, such as the prostate in this example, is then segmented (step 178) within the reconstructed 3D TAUS volume 176 by an automated segmentation method or manually by a radiologist. This segmentation step 178 results in the prostate contours 180 being marked or otherwise identified within the pre-biopsy reconstructed TAUS volume 176.

Once the pre-biopsy MR and TAUS contours are acquired, a surface-based deformable alignment (step 182) is performed using one or more suitable alignment routines to generate a pre-biopsy volume 184 in which the ultrasound and MR image data is aligned. This planning phase alignment may be based on at least the MR prostate contours 172, and the TAUS contours 180. In alignment step 182, the MR prostate contours 172 are aligned with the TAUS prostate contours 180, and these aligned prostate contours are integrated with, in the present example, the MR lesion contours 168. Implementing a surface-based alignment algorithm helps take into account the pre-biopsy deformation of the anatomy of interest (e.g. the prostate), and thus may help in aligning the pre-biopsy MR contours and pre-biopsy TAUS contours. Further, alignment accuracy of the pre-biopsy MR contours and pre-biopsy TAUS contours may be improved as a result of the simultaneous or near simultaneous acquisition, such as in temporally consecutive scans of the slices and volumes. As a result of the surface-based deformable alignment, the pre-biopsy TAUS volume 184, in which the TAUS prostate contours 180 are aligned with the MR prostate contours 172 and in which are integrated the MR lesion contours 168, is created.

As part of the planning phase, a deformable transformation model 188 is also generated to account for the movement of the prostate itself or deformation of the prostate induced by movement of surrounding organs or by physiological functions. In this example, a deep learning, patient-specific transformation model may be trained (step 186) based at least in part on the pre-biopsy TAUS volumes 174 to capture the range of motion of the pre-biopsy TAUS volumes 174. The resulting deformation transformation model 188 captures the range of prostate motion within the pre-biopsy TAUS volumes and may be used subsequently to help map subsequent ultrasound volumes to the pre-biopsy volume 184 to which the MR volume 164 and lesion contours 168 are mapped.

Turning to FIG. 5. during the biopsy phase, 3D biopsy TAUS volumes 194 are acquired (step 192) using the MR-compatible, 3D probe, which may be left in place from the pre-biopsy acquisitions, or another suitable probe. The 3D biopsy TAUS volumes may entail longitudinal volume frames and be a part of a biopsy ultrasound image data. A deformable alignment step 196 may be performed between the TAUS volumes 194 acquired during the biopsy and the pre-biopsy volumes. For example, the alignment performed at step 196 during the biopsy phase may utilize the 3D biopsy TAUS volume(s) 194, the deformable transformation model 188 from the planning phase, and the pre-biopsy volume 184, in which TAUS prostate contours 180 are aligned with MR prostate contours 172 and integrated with MR lesion contours 168. Deformable alignment 196 results in a real-time biopsy TAUS volume 198, in which the MR prostate contours 172 and/or lesion contours 168 are overlaid on (or otherwise displayed with) the TAUS volume 194 acquired during the biopsy.

Based on the real-time, transformed images, guidance may be provided, such as by an image acquisition and/or analysis system as described herein, to a surgeon or pathologist during or after a biopsy to facilitate the biopsy and/or to evaluate post-biopsy procedures. For instance, such guidance may include displaying an image or sequence of images based on the real-time, transformed images (block 198) which the surgeon or pathologist may reference in performing the biopsy or evaluating the biopsy. In other contexts, virtual or augmented reality techniques, for example, may display one or more lesion on the images displayed for the surgeon or pathologist.

Technical effects of the disclosed embodiments include providing systems and methods related to automatic multi-modal imaging that utilizes anatomic segmentation to facilitate accurate guidance in real-time tracking of moving, i.e., dynamic, anatomic objects. In particular, in one embodiment pre-biopsy ultrasound volumes are used to create a deformable transformation model to eventually assist in overlaying pre-biopsy MRI to a biopsy ultrasound domain. Such alignment based on deformable transformation is faster, more accurate, and robust to intensity variations and ultrasound imaging artifacts often encountered in routine medical procedure. Furthermore, in one embodiment an MR-compatible ultrasound probe is used for simultaneous acquisition of MRI and ultrasound in pre-biopsy stage. Such an acquisition improves the image alignment accuracy and allows better initialization for the subsequent deformable image alignments. The pre-biopsy MRI images, when adequately deformed using real-time ultrasound for guidance, may result in high tissue contrast visualization of the progress of the surgical resection procedure.

The technologies in this disclosure may be suitable to other problems related to automatic structure-guided rigid, affine, or deformable alignment. The structure to be aligned can be automatically segmented using a deformable transformation model.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A multi-modal imaging method to generate a patient-specific transformation model, comprising the steps of:
   acquiring pre-biopsy magnetic resonance (MR) image data and pre-biopsy ultrasound image data of a patient;

segmenting an anatomic region of interest and one or more lesions in an MR volume generated from the pre-biopsy MR image data;

segmenting the anatomic region of interest in an ultrasound volume generated from ultrasound image data;

aligning contours of the segmented anatomic region of interest in the MR volume with corresponding contours of the anatomic region of interest in the ultrasound volume to generate a pre-biopsy volume in which the MR volume and the ultrasound volume are aligned and on which contours of the one or more lesions from the MR volume are aligned;

training a deep learning transformation model based at least in part on the pre-biopsy ultrasound image data to create a deformable transformation model specific to the patient;

wherein the pre-biopsy ultrasound image data comprise longitudinal volume frames; and wherein a range of motion of the pre-biopsy longitudinal volume frames is captured by the deep learning transformation model.

2. The method of claim 1, wherein the pre-biopsy MR image data comprises two-dimensional (2D) MR images reconstructed into a 3D representation and the pre-biopsy ultrasound image data comprises three-dimensional (3D) ultrasound images acquired over time.

3. The method of claim 1, wherein the deep learning transformation model is specific to the anatomic region of interest.

4. The method of claim 3, wherein the anatomic region of interest comprises a prostate.

5. The method of claim 1, wherein the pre-biopsy MR image data and pre-biopsy ultrasound image data are acquired simultaneously.

6. The method of claim 5, wherein the pre-biopsy ultrasound image data is acquired using an MR compatible ultrasound probe.

7. The method of claim 1, further comprising the steps of:

acquiring one or more biopsy ultrasound images of a patient during a biopsy procedure;

performing a deformable alignment using the deformable transformation model to align each biopsy ultrasound image with the pre-biopsy volume, wherein the contours of the one or more lesions are previously associated with each biopsy ultrasound image; and providing a real-time visualization of the contours of the one or more lesions on some or all of the biopsy ultrasound images.

8. A multi-modal imaging system comprising:

a memory encoding processor-executable routines; and a processing component configured to access the memory and execute the processor-executable routines, wherein the routines, when executed by the processing component, cause the processing component to perform actions comprising:

acquiring pre-biopsy magnetic resonance (MR) image data and pre-biopsy ultrasound image data of a patient;

segmenting an anatomic region of interest and one or more lesions in an MR volume generated from the pre-biopsy MR image data;

segmenting the anatomic region of interest in an ultrasound volume generated from the ultrasound image data;

aligning contours of the segmented anatomic region of interest in the MR volume with corresponding contours of the anatomic region of interest in the ultrasound volume to generate a pre-biopsy volume in which the MR volume and the ultrasound volume are aligned and on which contours of the one or more lesions from the MR volume are aligned;

training a deep learning transformation model based at least in part on the pre-biopsy ultrasound image data to create a deformable transformation model specific to the patient;

acquiring one or more biopsy ultrasound images of the patient during a biopsy procedure;

performing a deformable alignment using the deformable transformation model to align each biopsy ultrasound image with the pre-biopsy volume, wherein the contours of the one or more lesions are associated with each biopsy ultrasound image;

providing a real-time visualization of the contours of the one or more lesions on some or all of the biopsy ultrasound images;

wherein the pre-biopsy ultrasound image data comprise longitudinal volume frames; and wherein a range of motion of the pre-biopsy longitudinal volume frames is captured by the deep learning transformation model.

9. The method of claim 8, wherein the pre-biopsy MR image data comprises two-dimensional (2D) MR images reconstructed into a 3D representation and the pre-biopsy ultrasound image data comprises three-dimensional (3D) ultrasound images.

10. The method of claim 8, wherein the deep learning transformation model is specific to the anatomic region of interest.

11. The method of claim 8, wherein the pre-biopsy MR image data and pre-biopsy ultrasound image data are acquired simultaneously.

12. A method to register a real-time image for a biopsy system, comprising the steps of:

acquiring one or more biopsy ultrasound images of a patient during a biopsy procedure;

performing a deformable alignment using a deformable transformation model to align each biopsy ultrasound image with a pre-biopsy volume, wherein the deformable transformation is specific to the patient and wherein the contours of one or more lesions are associated with each biopsy ultrasound image;

providing a real-time visualization of the contours of the one or more lesions on some or all of the biopsy ultrasound images;

wherein the deformable transformation model is generated using a deep learning transformation model trained at least in part based on pre-biopsy ultrasound image data;

wherein the pre-biopsy ultrasound image data comprise longitudinal volume frames; and wherein a range of motion of the pre-biopsy longitudinal volume frames is captured by the deep learning transformation model.

13. The method of claim 12, wherein the biopsy procedure comprises a trans-perineal biopsy procedure.

14. The method of claim 12, wherein the deep learning transformation model is specific to the anatomy of interest.

* * * * *